United States Patent [19]
Kurokawa et al.

[11] Patent Number: 5,294,719
[45] Date of Patent: Mar. 15, 1994

[54] CYCLOHEXYLAMINE COMPOUNDS USEFUL AS A STABILIZER FOR ORGANIC MATERIALS

[75] Inventors: Hideki Kurokawa; Mitsumasa Kaitoh; Akiyoshi Ohnishi, all of Yokkaichi, Japan

[73] Assignee: Mitsubishi Petrochemical Company Limited, Tokyo, Japan

[21] Appl. No.: 996,026

[22] Filed: Dec. 23, 1992

[30] Foreign Application Priority Data

Dec. 26, 1991 [JP] Japan .................. 3-357513

[51] Int. Cl.$^5$ .................. C07D 211/46; C07D 401/12
[52] U.S. Cl. .................. 546/188; 546/187; 546/214; 546/222
[58] Field of Search .................. 546/187, 188, 214, 222

[56] References Cited

U.S. PATENT DOCUMENTS

| | | | |
|---|---|---|---|
| 4,102,858 | 7/1978 | Minagawa et al. | 546/188 |
| 4,670,488 | 6/1987 | Maegawa et al. | 546/188 |
| 4,670,489 | 6/1987 | Takahashi et al. | 546/188 |
| 5,026,750 | 6/1991 | Ravichandran | 546/188 |

FOREIGN PATENT DOCUMENTS

| | | | |
|---|---|---|---|
| 0107805 | 5/1984 | European Pat. Off. | |
| 127356 | 12/1984 | European Pat. Off. | 546/188 |
| 0211572 | 2/1987 | European Pat. Off. | |
| 1032646 | 6/1966 | United Kingdom | 546/222 |

*Primary Examiner*—C. Warren Ivy
*Assistant Examiner*—Celia Chang

*Attorney, Agent, or Firm*—Oblon, Spivak, McClelland, Maier & Neustadt

[57] ABSTRACT

Compounds useful as a stabilizer for a variety of organic materials of an intermediate thereof, or as an intermediate of medicines or agricultural chemicals are disclosed, which are cyclohexylamine derivatives represented by the general formula [I]:

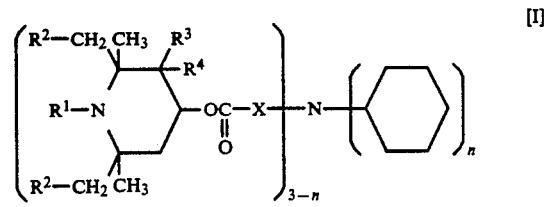

wherein $R^1$ represents a hydrogen atom, an alkyl group having 1 to 4 carbon atoms, an acyl group having 2 to 7 carbon atoms or an arylalkyl group having 7 to 10 carbon atoms; $R^2$ represents a hydrogen atom or an alkyl group having 1 to 4 carbon atoms; $R^3$ and $R^4$ both represent a hydrogen atom, or one of $R^3$ and $R^4$ represents a hydrogen atom and the other represents a group —$CH_2$—$R^5$, or $R^3$ and $R^4$ together form a group =CH—$R^5$, in which $R^5$ represents an unsubstituted or $C_1$-$C_4$ alkyl substituted phenyl group, a 2-furyl group, a cyclohexyl group or a 2-tetrahydrofuryl group; X represents an alkylene group having 1 to 3 carbon atoms; and n denotes 1 or 2.

When the compound is used as a stabilizer, it exhibits little bleedout and high photostabilizing effect.

15 Claims, 2 Drawing Sheets

CYCLOHEXYLAMINE COMPOUNDS USEFUL AS A STABILIZER FOR ORGANIC MATERIALS

BACKGROUND OF THE INVENTION

1. Field of the Invention

The present invention relates to a cyclohexylamine derivative having a novel structure, more particularly a cyclohexylamine derivative having 2,2,6,6-tetramethylpiperidine structure which is useful as a photostabilizer for variety of organic materials or as an intermediate thereof and can be used also as an intermediate of medicines or agricultural chemicals.

2. Prior Art

It has hitherto been known that compounds having a 2,2,6,6-tetraalkylpiperidine structure (the so-called hindered amine structure) possess an excellent radical-capturing ability, and they have been used as a photostabilizer of organic materials, particularly resins by taking advantage of the property.

For example, bis(2,2,6,6-tetramethyl-4-piperidinyl)-sebacate of formula (1) (trade name: SANOL ® LS770, referred to hereinafter as LS770) which is one of the typical photostabilizers, as described in "Recent Technology of Polymer Additives" by Yutaka Nakahara, CMC Co., 1988, is known to be an ester of 2,2,6,6-tetramethyl-4-piperidinol and sebacic acid and to exhibit high photostabilizing effect on many resins such as polyolefins and the like.

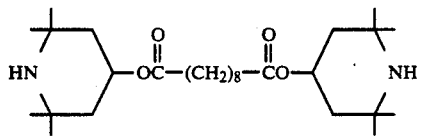
(1)

LS770 with a high photostabilizing effect can, however, bleed out from resins to which it has been added during its use and thus has problems that it can hardly be used for thin products such as film or the like, or may affect deleteriously a coating on the surface of a relatively thick product of a resin to which it has been added during its use for a long period.

Recently, a photostabilizer afforded with high molecular weight such as of formula (2) (trade name: CHIMASSORB ® 944) has been developed in order to settle the problem of bleedout as described above.

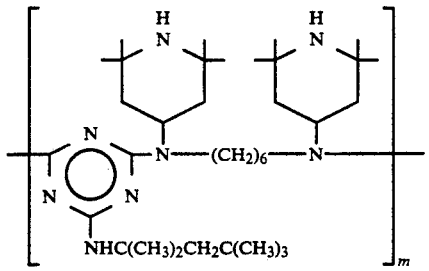
(2)

The compound, notwithstanding the absence of the bleedout from resins, has only an insufficient effect on photostabilization.

The present inventors have conducted researches on settling the problems described above, resulting in the discovery of a new cyclohexylamine derivative represented by the general formula [I] which can be produced industrially, has a high photostabilizing effect and exhibits little bleedout from resins when used as a photostabilizer.

SUMMARY OF THE INVENTION

The object of the present invention is to solve the problems recognized in the aforementioned prior art by providing a compound having a particular molecular structure.

The cyclohexylamine derivative according to the present invention is the compound represented by the general formula [I]:

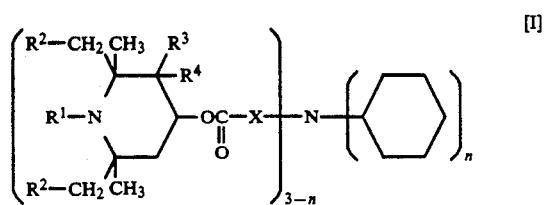
[I]

wherein $R^1$ represents a hydrogen atom, an alkyl group having 1 to 4 carbon atoms, an acyl group having 2 to 7 carbon atoms or an arylalkyl group having 7 to 10 carbon atoms, and $R^2$ each represents a hydrogen atom or an alkyl group having 1 to 4 carbon atoms, $R^3$ and $R^4$ both represent a hydrogen atom, or one of $R^3$ and $R^4$ represents a hydrogen atom and the other represents a group $—CH_2—R^5$, or $R^3$ and $R^4$ together form a group $=CH—R^5$, in which $R^5$ represents an unsubstituted or $C_1$-$C_4$ alkyl substituted phenyl group, a 2-furyl group, a cyclohexyl group or a 2-tetrahydrofuryl group, X represents an alkylene group having 1 to 3 carbon atoms, and n denotes 1 or 2.

The cyclohexylamine derivatives according to the present invention possess cyclohexyl groups in the molecule and thus has excellent properties as compared with the conventional photostabilizers that it is highly compatible with a variety of organic materials such as resins, particularly polyolefins, for example, polyethylene, polypropylene, polystyrene or the like and that when it is used as a photostabilizer for polyolefins, it exhibits little bleedout from the resin and thus has a high photostabilizing effect.

DETAILED DESCRIPTION OF THE PREFERRED EMBODIMENT OF THE INVENTION

Compound

Figure 1:
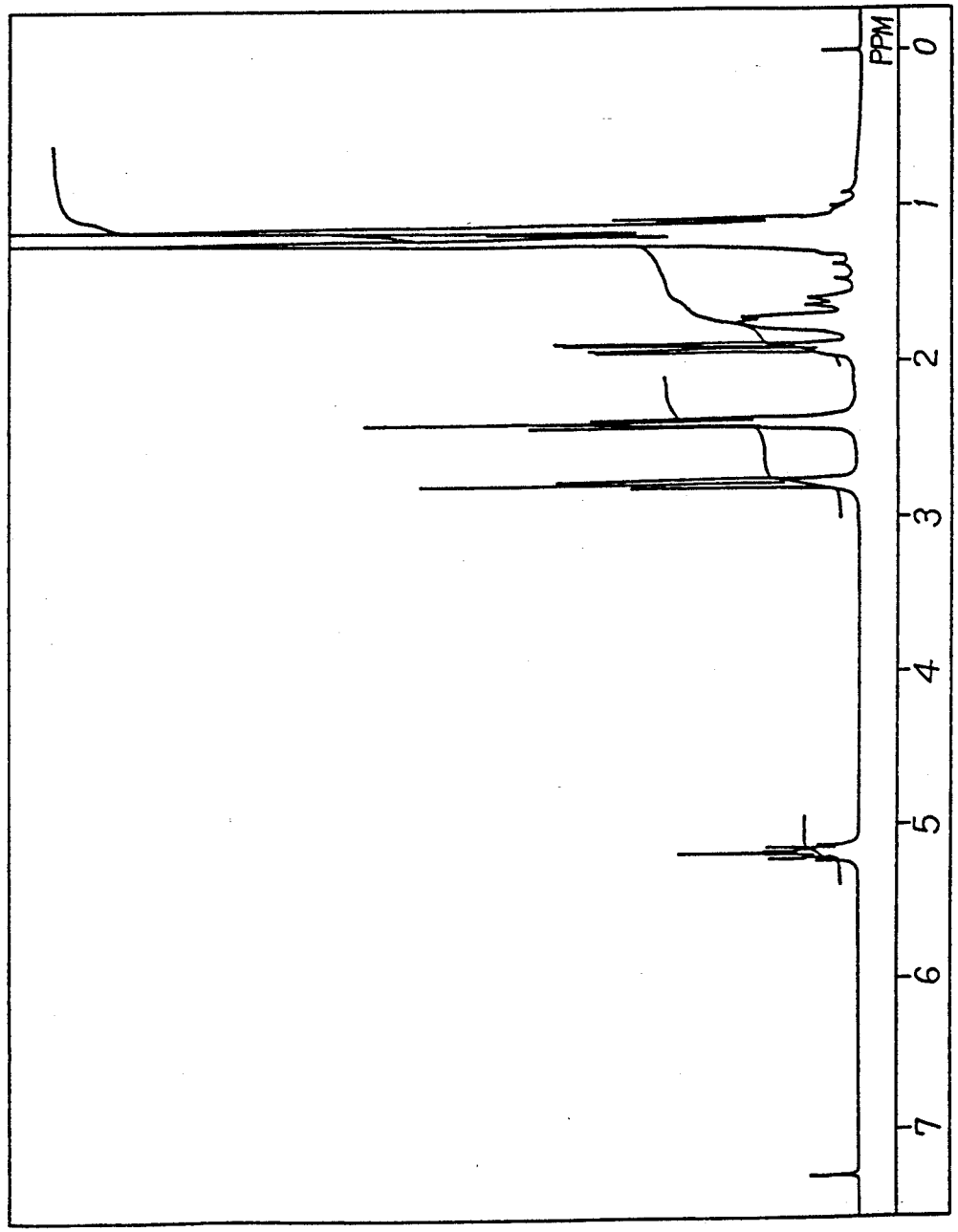
FIG. 1 shows a $^1$H-NMR spectrum of N,N-bis[2-(2,2,6,6-tetramethyl-4-piperidinyloxycarbonyl)ethyl]-cyclohexylamine prepared in Example 1.
Figure 2:
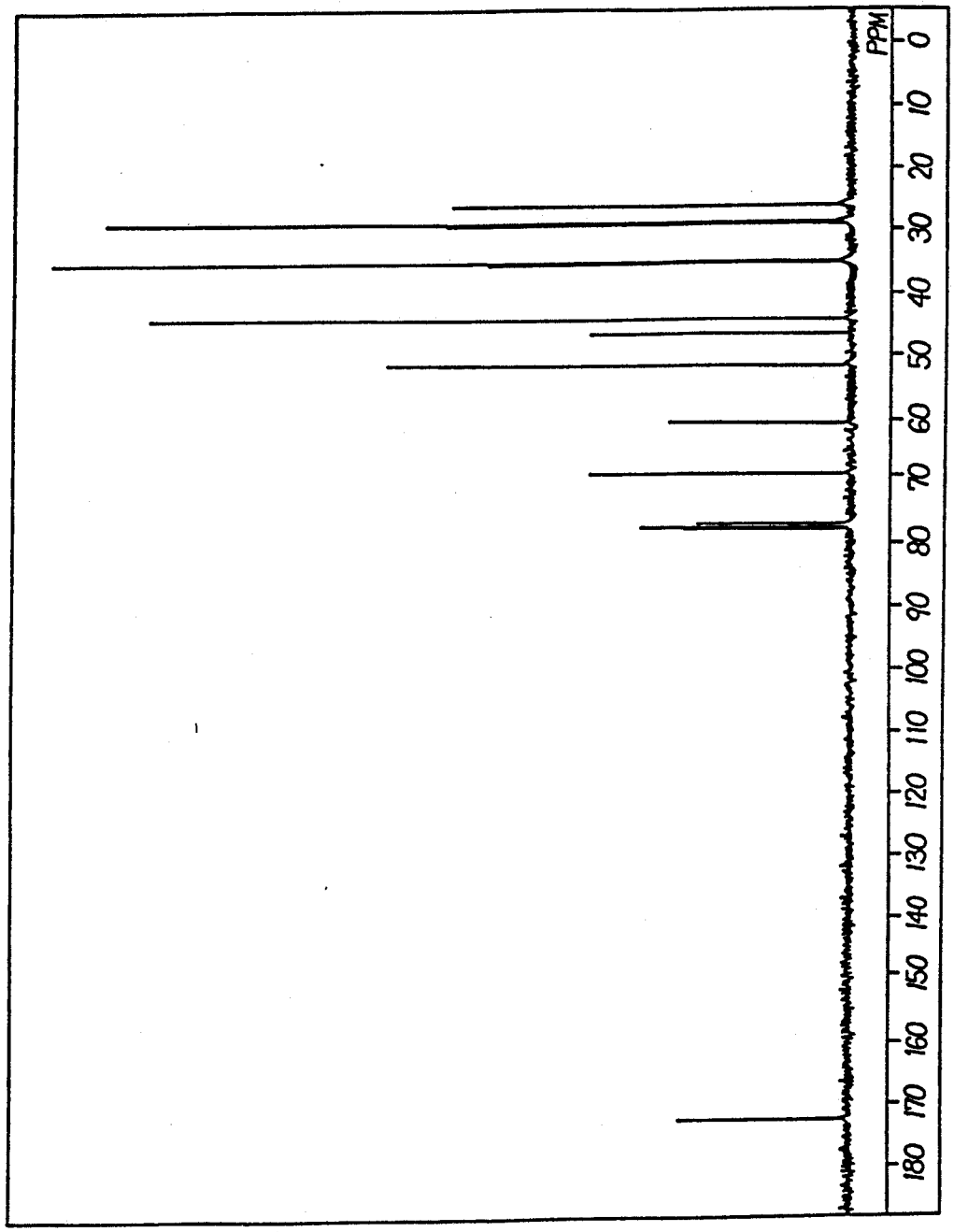
FIG. 2 shows a $^{13}$C-NMR spectrum (proton decoupling method) of N,N-bis[2-(2,2,6,6-tetramethyl-4-piperidinyloxycarbonyl)ethyl] cyclohexylamine prepared in Example 1.

The cyclohexylamine derivatives according to the present invention are represented by the general formula [I], wherein $R^1$ may be optionally selected from (i) a hydrogen atom, (ii) an alkyl group having 1 to 4 carbon atoms such as a methyl group, a n-butyl group or the like, (iii) an acyl group having 2 to 7 carbon atoms of the formula —C(=O)—R$^6$, in which R$^6$ represents a C$_1$–C$_6$ alkyl group or a phenyl group, such as an acetyl group, a benzoyl group or the like, or (iv) an phenylalky group having 7 to 10 carbon atoms of the formula

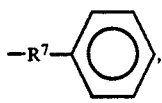

in which R$^7$ represents a C$_1$–C$_4$ alkylene group, such as a benzyl group, 1-phenylethyl group or the like, and either of these derivatives may exhibit similar photostabilizing effect. R$^1$ is preferably a hydrogen atom or a methyl group, particularly a hydrogen atom, in view of the production of the compounds of the present invention. On the other hand, when R$^1$ represents a hydrogen atom, the compounds of the present invention exhibits relatively strong basicity. Thus, when the compound of the present invention is used in the presence of acidic paints or other additives, a group other than a hydrogen atom such as a methyl group, an acetyl group or a benzoyl group is preferably selected for R$^1$ in consideration of the photostabilizing effect, dispersibility, compatibility and bleedout.

R$^2$ may be selected from (i) a hydrogen atom, and (ii) an alkyl group having 1 to 4 carbon atoms such as a methyl group or a n-butyl group, among which a hydrogen atom or a methyl group, particularly a hydrogen atom, is preferred.

R$^3$ and R$^4$ (i) both represent a hydrogen atom, (ii) one of R$^3$ and R$^4$ represents a hydrogen atom and the other represents a group —CH$_2$—R$^5$, or (iii) R$^3$ and R$^4$ together form a group =CH—R$^5$, in which R$^5$ represents (a) a phenyl group, (b) a C$_1$–C$_4$ alkyl substituted phenyl group such as tolyl group or a p-t-butyl group, (c) a 2-furyl group, (d) a cyclohexyl group or (e) a 2-tetrahydrofuryl group. In this connection, the position of the substituent in the alkyl substituted phenyl group (b) may be at any positions of the aromatic ring. Among these groups of R$^3$ and R$^4$, the groups in which (1) both of R$^3$ and R$^4$ represent a hydrogen atom, (2) R$^3$ represents a hydrogen atom and R$^4$ represents a benzyl group, and (3) R$^3$ represents a hydrogen atom and R$^4$ represents a cyclohexylmethyl group are preferred and the groups in which (1) both of R$^3$ and R$^4$ represents a hydrogen atom is particularly preferred.

X represents a C$_1$–C$_3$ alkylene group such as —CH$_2$—, —CH$_2$CH$_2$— or —CH(CH$_3$)CH$_2$—. Among these groups, —CH$_2$CH$_2$— is preferable as X.

n denotes 1 or 2. Among these integers, n preferably denotes 1.

The cyclohexylamine derivatives according to the present invention are, as apparent from the formula [I], compounds having basicity due to the cyclohexylamine and due to the piperidine ring when R$^1$ represents a hydrogen atom, an alkyl group or an arylalkyl group, and thus the cyclohexylamine derivatives according to the present invention include their acid addition salts. Thus, the "cyclohexylamine derivatives" herein also include their acid addition salts. Acids which can form acid addition salts with cyclohexylamine and piperidine are well known and can be selected appropriately from organic acids and inorganic acids in the present invention. Specific examples include, for example, (i) organic acids such as mono-, di- or polycarboxylic acids and (ii) inorganic acids such as hydrochloric acid, sulfuric acid, phosphoric acid or the like.

Typical examples of the cyclohexylamine derivatives represented by the general formula [I] according to the present invention include:

1) N,N-bis[2-(2,2,6,6-tetramethyl-4-piperidinyloxycarbonyl)ethyl]cyclohexylamine
   (Illustrative Compound 1),

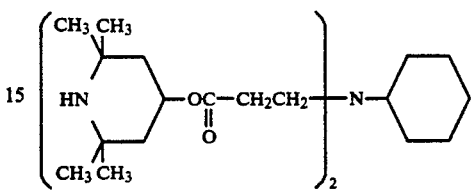

2) N,N-bis[2-(1,2,2,6,6-pentamethyl-4-piperidinyloxycarbonyl)ethyl]cyclohexylamine
   (Illustrative Compound 2),

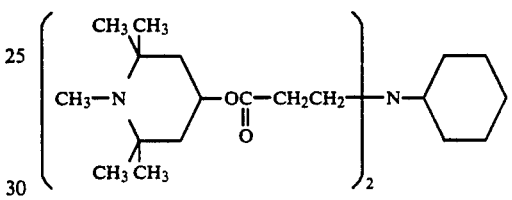

3) N,N-bis[2-(1-acetyl-2,2,6,6-tetramethyl-4-piperidinyloxycarbonyl)ethyl]cyclohexylamine
   (Illustrative Compound 3),

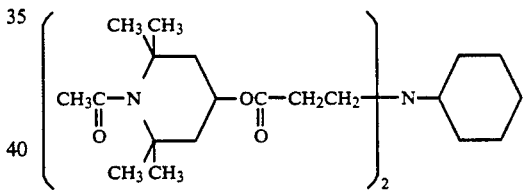

4) N,N-bis[2-(1-benzyl-2,2,6,6-tetramethyl-4-piperidinyloxycarbonyl)ethyl]cyclohexylamine
   (Illustrative Compound 4),

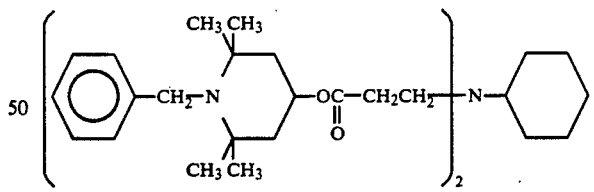

5) N,N-bis[2-(1-benzoyl-2,2,6,6-tetramethyl-4-piperidinyloxycarbonyl)ethyl]cyclohexylamine
   (Illustrative Compound 5),

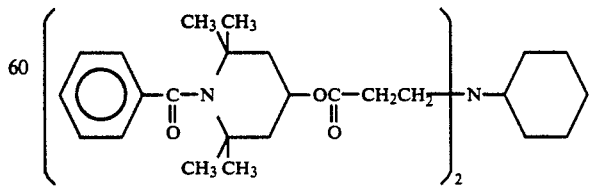

6) N,N-bis[2-(3-benzyl-2,2,6,6-tetramethyl-4-piperidinyloxycarbonyl)ethyl]cyclohexylamine
   (Illustrative Compound 6),

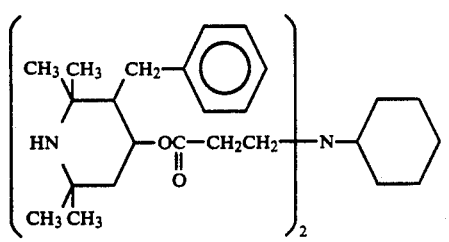

7) N,N-bis[2-(3-cyclohexylmethyl-2,2,6,6-tetramethyl-4-piperidinyloxycarbonyl)ethyl]cyclohexylamine (Illustrative Compound 7),

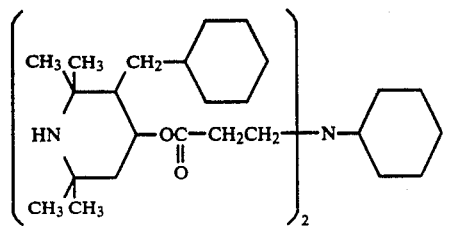

8) N,N-bis{2-[3-(2-furfuryl)-2,2,6,6-tetramethyl-4-piperidinyloxycarbonyl)ethyl]cyclohexylamine (Illustrative Compound 8),

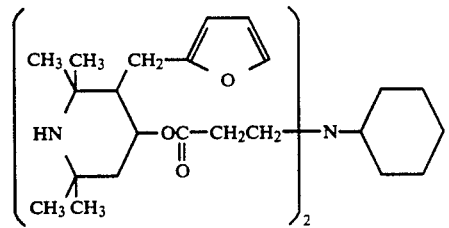

9) N,N-bis[2-(3-benzyl-1,2,2,6,6-pentamethyl-4-piperidinyloxycarbonyl)ethyl]cyclohexylamine (Illustrative Compound 9),

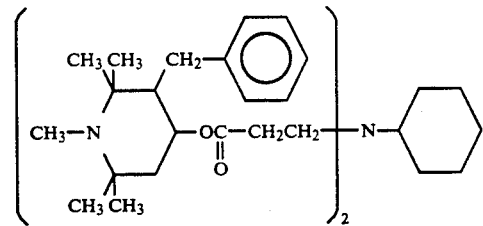

10) N,N-bis[2-(3-cyclohexylmethyl-1,2,2,6,6-pentamethyl-4-piperidinyloxycarbonyl)ethyl]cyclohexylamine (Illustrative Compound 10),

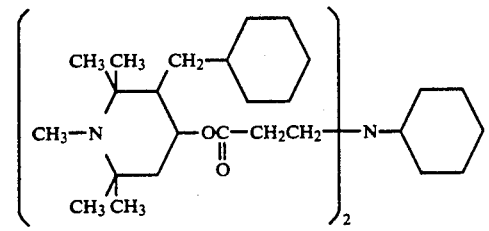

11) N,N-bis[2-(1-acetyl-3-benzyl-2,2,6,6-tetramethyl-4-piperidinyloxycarbonyl)ethyl]cyclohexylamine (Illustrative Compound 11),

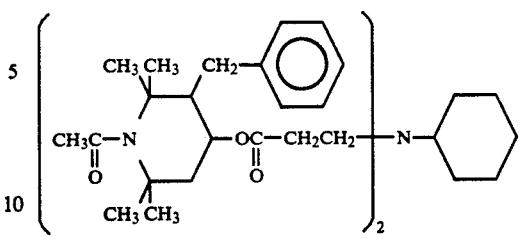

12) N,N-bis[2-(1-acetyl-3-cyclohexylmethyl-2,2,6,6-tetramethyl-4-piperidinyloxycarbonyl)ethyl]-cyclohexylamine (Illustrative Compound 12),

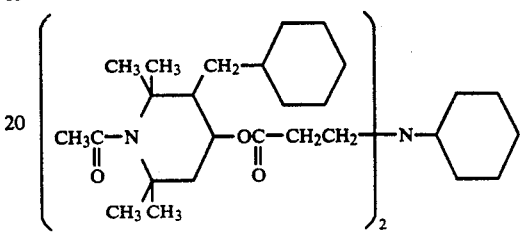

13) N-[2-(2,2,6,6-tetramethyl-4-piperidinyloxycarbonyl)-ethyl]dicyclohexylamine (Illustrative Compound 13),

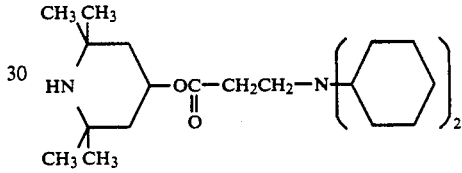

14) N-[2-(1,2,2,6,6-pentamethyl-4-piperidinyloxycarbonyl)ethyl]dicyclohexylamine (Illustrative Compound 14),

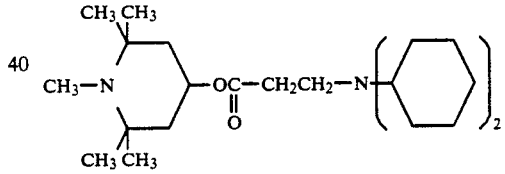

15) N-[2-(1-acetyl-2,2,6,6-tetramethyl-4-piperidinyloxycarbonyl)ethyl]dicyclohexylamine (Illustrative Compound 15),

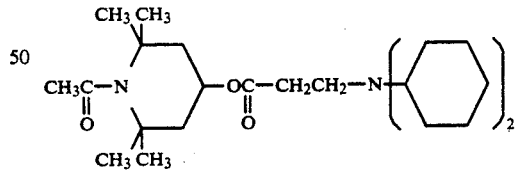

16) N-[2-(1-benzyl-2,2,6,6-tetramethyl-4-piperidinyloxycarbonyl)ethyl]dicyclohexylamine (Illustrative Compound 16),

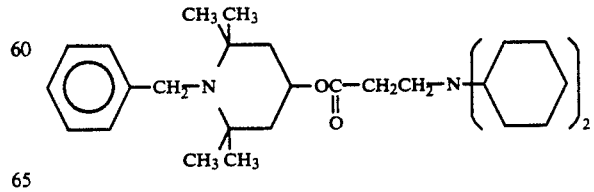

17) N-[2-(3-benzyl-2,2,6,6-tetramethyl-4-piperidinyloxycarbonyl)ethyl]dicyclohexylamine (Illustrative Compound 17),

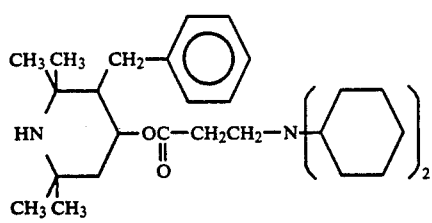

18) N-[2-(3-cyclohexylmethyl-2,2,6,6-tetramethyl-4-piperidinyloxycarbonyl)ethyl]dicyclohexylamine (Illustrative Compound 18),

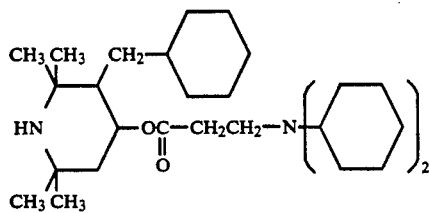

19) N,N-bis(2,2,6,6-tetramethyl-4-piperidinyloxycarbonylmethyl)cyclohexylamine (Illustrative Compound 19),

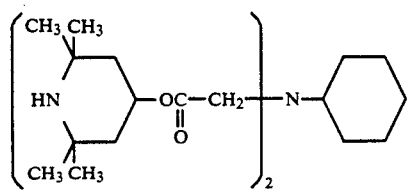

20) N,N-bis[2-methyl-2-(2,2,6,6-tetramethyl-4-piperidinyloxycarbonyl)ethyl]cyclohexylamine (Illustrative Compound 20),

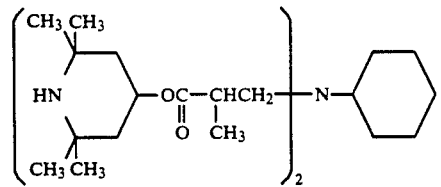

21) N,N-bis(1,2,2,6,6-pentamethyl-4-piperidinyloxycarbonylmethyl)cyclohexylamine (Illustrative Compound 21),

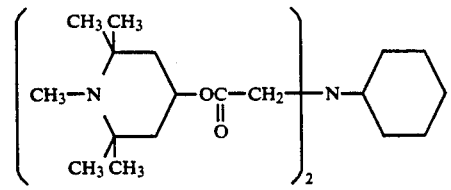

22) N,N-bis[2-methyl-2-(1,2,2,6,6-pentamethyl-4-piperidinyloxycarbonyl)ethyl]cyclohexylamine (Illustrative Compound 22),

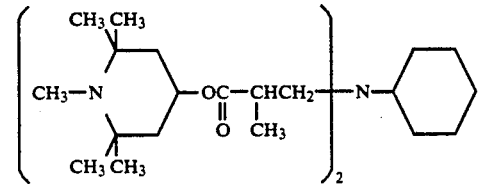

Production of the compounds

The cyclohexylamine derivatives of the present invention can be produced by any appropriate methods for the formation of bonds or groups in the compound. Some of the typical production methods may be illustrated below:

(1) Addition of the α,β-unsaturated carboxylate compound to the amine compound to form an aminated carboxylate compound ([Reaction 1]) and esterification reaction of the aminated carboxylate with the piperidinol derivative ([Reaction 2])

When X is —CH$_2$CH$_2$— or —CH(CH$_3$)CH$_2$—, the cyclohexylamine derivatives of the present invention can be prepared according to the following scheme 1.

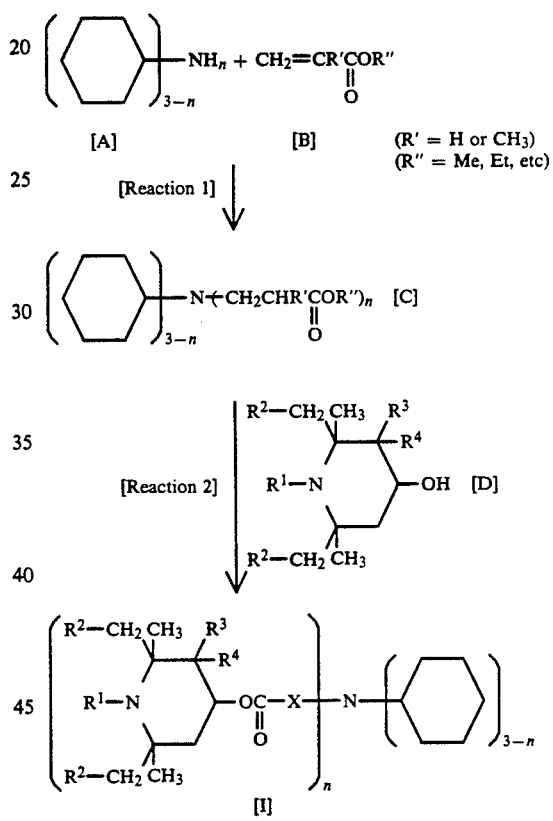

Reaction 1 of Scheme 1 is a Michael type addition reaction of the amine compound [A] to the α,β-unsaturated carboxylate compound [B]. Specifically, cyclohexylamine (n=2 in the formula) or dicyclohexylamine (n=1) as the amine compound [A] and methyl acrylate, ethyl acrylate, methyl methacrylate or ethyl methacrylate as the α,β-unsaturated carboxylate compound [B] are reacted without solvent or in an appropriate solvent in the absence of catalyst or in the presence of an appropriate catalyst. When the reaction is conducted in a solvent, any solvent can be used. However, if an α,β-unsaturated ester (CH$_2$=CR'CO$_2$R") is used as the α,β-unsaturated carboxylate compound [B] and an alcohol is used as the solvent, the alcohol solvent is preferably R"OH (e.g. if methyl acrylate is used as the α,β-unsaturated ester, methanol is used as the solvent).

The reaction is usually conducted with the α,β-unsaturated carboxylate compound in an amount of 1 to 10 times, preferably 1 to 5 times, more preferably 1 to 3 times, the amount of the amine compound [A]. In this connection, the unreacted α,β-unsaturated carboxylate compound [B] is removed by distillation or another procedure after the completion of the reaction and is employed again for the reaction. After the reaction, the target compound with high purity is easily obtained by the treatment such as distillation, if the reaction is exhaustively progressed with an excessive amount of the α,β-unsaturated compound [B], whereby the target compound is usually obtained in a purity of 95% or more upon removal of the unreacted α,β-unsaturated compound [B].

Catalyst is not required for the reaction, but acetic acid may be appropriately used as the catalyst if satisfactory reaction rate is not obtained. Although the reaction temperature is not limited to specific levels, the reaction is generally carried out at a reflux temperature of the reaction mixture. If the reaction progresses very slowly, it is conducted at a temperature of reflux or more in a pressurized reactor.

Reaction 2 is a transesterification reaction between the compound [D] which is a piperidinol derivative and the compound [C] obtained in Reaction 1 which can be in a crude or purified state. The reaction may be carried out in the presence of a catalyst in a solvent while an alcohol resulting from the reaction is removed.

In the reaction, the compound [D] is used in an amount of 1.0 to 1.5 times, preferably 1.0 to 1.2 times, the amount of the compound [C] in order that the transesterification reaction may fully proceed. After the reaction has been completed, the unreacted piperidinol compound [D] is removed by a treatment such as recrystallization or extraction with an appropriate solvent to yield the desired compound [I] in high purity. When the compound [I] is used as a stabilizer for organic materials, it can be used directly without purification unless the unreacted piperidinol compound [D] affects deleteriously the organic materials (in this connection, the term "affects deleteriously" means not only the lowering of the function of the compound [I] as a stabilizer but also the lowering of physical or chemical properties required for the organic materials under use).

As the catalyst, an acid or base catalyst used for general esterification or transesterification reactions can be used. For example, (i) as the acid catalyst, mineral acids such as hydrochloric acid or sulfuric acid, metal alkoxides such as tetraisopropoxytitanium (IV) or triisopropoxyaluminum (III), heteropolyacids such as 12tungstophosphoric acid or 12molybdosilicic acid, oxides such as crystalline or amorphous silica-alumina, or the like are used; (ii) as the base catalyst, alkali or alkaline earth metal hydroxides such as sodium hydroxide or calcium hydroxide, alkali or alkaline earth metal alkoxides such as sodium methoxide or magnesium methoxide, alkali or alkaline earth metal amides such as lithium amide or sodium amide, oxides such as magnesium oxide or calcium oxide, or the like are used. Among these catalysts, tetraisopropoxytitanium (IV), triisopropoxyaluminum (III), sodium methoxide or lithium-amide are preferred, and particularly lithiuma-mide is more preferred.

The solvent is appropriately selected depending upon combinations of the solubilities of reactants, catalysts, reaction temperatures or the other factors, and aliphatic hydrocarbons such as hexane or heptane, aromatic hydrocarbons such as benzene, toluene or xylene, or the like are usually used. Preferable solvents are those which form an azeotropic mixture with an alcohol ($R^6OH$) resulting from the reaction and desirably cause phase separation from the alcohol ($R^6OH$) at ambient temperature whereby the alcohol $R^6OH$ resulting from the reaction can be continuously removed from the reaction system with use of a separation system of the Dean Stark type. If no phase separation takes place, the alcohol $R^6OH$ may be removed from a mixture taken out from the reaction system by distillation or with an adsorbent. Among these solvents, hexane, heptane and toluene are preferred, and particularly heptane is more preferred.

The reaction temperature varies depending upon the reactants and solvents used, and the reaction is generally carried out at a temperature in the range of 50° to 150° C.

(2) Reaction of the amine compound and the halocarboxylate compound ([Reaction 3]) to form an aminated carboxylate compound and esterification reaction of the aminated carboxylate compound with the piperidinol derivative ([Reaction 4])

When X represents —$CH_2$—, the production process described in the following scheme 2 is particularly useful.

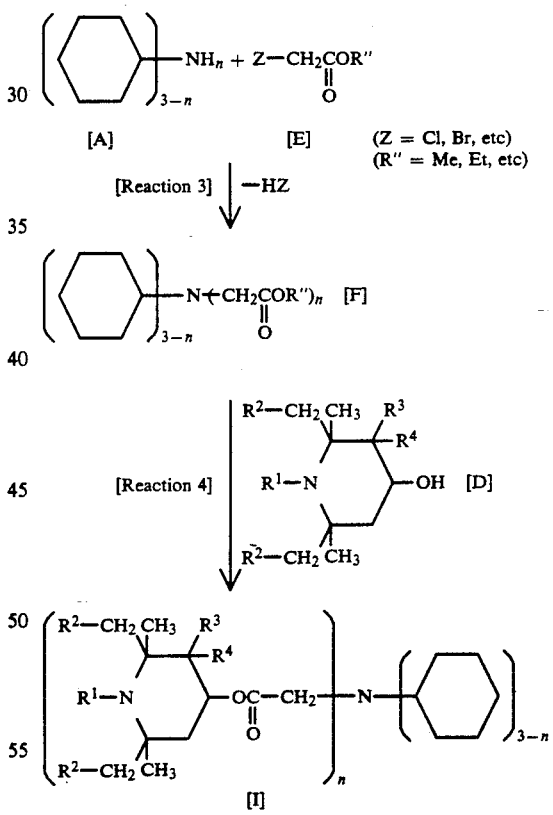

The reaction [3] is a dehydrohalogenation reaction between the amine compound [A] and the halocarboxylate compound [B]. Specifically, cyclohexylamine (n=2 in the formula A) or dicyclohexylamine (n=1) as the amine compound [A] and methyl chloroacetate or ethyl chloroacetate are reacted in the presence or absence of a dehydrohalogenation agent.

As the dehydrohalogenation agent, tertiary amines such as pyridine or triethylamine, basic inorganic salts such as sodium carbonate or potassium carbonate, or basic inorganic compounds such as calcium hydroxide or magnesium hydroxide are used. These dehydrohalogenation agents are generally used in an amount of 1 to 5 times, preferably 1 to 3 times, the amount of the hydrogen halide resulting from the reaction.

The reaction solvent may be used according to necessities, and aliphatic or aromatic hydrocarbons such as hexane, cyclohexane, benzene or xylene, or ethers such as dioxane or tetrahydrofuran are generally used. If a liquid dehydrohalogenation agent such as a tertiary amine, e.g. pyridine or triethylamine is used, the amine can be utilized as the solvent.

The reaction temperature is not particularly limited, but the reaction is generally carried out at a temperature in the range of 0° to 200° C., preferably 0° to 150° C.

Reaction 4 is the same reaction as Reaction 2 in the above described Scheme 1, and the target compound is obtained in the same manner as in Reaction 2.

Utility of the compound

The cyclohexylamine derivatives of the general formula [I] according to the present invention are useful as a photostabilizer for a variety of organic materials. Typical examples of the organic materials include poly-($\alpha$-olefin) such as low density polyethylene, high density polyethylene, linear low density polyethylene, polypropylene or polybutene-1; $\alpha$-olefin copolymers such as ethylene-propylene random or block copolymers or ethylene-(butene-1) random copolymers; copolymers of a poly($\alpha$-olefin) and a vinyl monomer such as maleic anhydride denaturated polypropylene; and mixtures thereof.

In addition to the above described organic materials, synthetic high molecular compounds to which the cyclohexylamine derivatives according to the present invention can be used for stabilization against light include styrene resins such as polystyrene, impact-resistant polystyrene, an ABS resin and an AES resin; polyvinyl chloride; acrylic and methacrylic resins; polyesters such as polyethylene terephthalate and polybutylene terephthalate; polyamides such as a nylon and the like; polycarbonates; polyacetals; polyethylene oxides; polyphenylene ethers; polysulfones; polyurethanes; unsaturated polyester resins and the like.

Natural organic compounds are also the objects stabilized by the compound of the present invention and specifically include celluloses, rubbers, proteins, natural polymers derived therefrom, mineral oils, animal or vegetable oils, waxes and the like.

The compound of the present invention, which is effective even when used alone, can be expected to have a higher effect by the use of it in combination with a variety of other stabilizers.

The present invention is specifically described in reference to the following examples.

Example 1

N,N-bis[2-(2,2,6,6-tetramethyl-4-piperidinyloxycarbonyl)-ethyl]cyclohexylamine (Illustrative Compound 1)

[Reaction 1]

To a 100 ml reactor equipped with a magnetic stirrer, a thermocouple and a condenser were added 9.9 g (100 mmol) of cyclohexylamine, 50 ml of methanol and 28.4 g (330 mmol, 1.65 equivalents) of methyl acrylate, and the reaction system was heated under ample stirring to 65° C. to conduct reaction at the temperature for 20 hours.

After the given reaction time, the reaction system was cooled to room temperature, and methanol and unreacted methyl acrylate were removed under reduced pressure. The procedure comprising the addition of 50 ml of methanol to the residue and the distillation under reduced pressure was repeated three times to remove completely the methyl acrylate.

The compound obtained was N,N-bis(2-methoxycarbonylethyl)cyclohexylamine (referred to hereinafter as CHADA) in an amount of 26.0 g (purity, 96%) and a yield of 92%.

Reaction 2]

To a 300 ml reactor equipped with a magnetic stirrer, a thermocouple and a Dean-Stark condenser were added 13.6 g (50 mmol) of CHADA (not purified) obtained in the [Reaction 1] described above, 17.3 g (110 mmol) of 2,2,6,6-tetramethyl-4-piperidinol, 200 ml of heptane and 0.2 g (8.7 mmol) of lithiumamide. The reaction system was heated under ample stirring to about 100° C. to conduct reaction for 12 hours with removal of methanol distilled by the Dean-Stark condenser. After the given reaction period, the reaction mixture cooled to room temperature was transferred to a separatory funnel, and 500 ml of ether was added before washing three times with 100 ml of $H_2O$. The solution after washing with water was dried over anhydrous magnesium sulfate for about 3 hours, filtered, concentrated to give 23.4 g of a white waxy solid (purity, 97.9%). Purification of the solid by chromatography on an alumina column (solvent, $CHCl_3$) gave 21.5 g of white crystals as the target compound (Illustrative Compound 1) (yield, 82.4%).

Physical properties of the compound are as follows:
(1) Melting point: 69.7° C.
(2) Molecular weight: 521 (m/e).
(3) $^1H$-NMR ($CDCl_3$) $\delta$ (ppm) 0.93–1.34 (m, 35H), 1.52–2.02 (m, 9H), 2.27–2.52 (m, 5H), 2.78 (t, 4H), 5.07–5.33 (m, 2H).
(4) $^{13}C$-NMR ($CDCl_3$) $\delta$ (ppm) 26.1, 26.3, 29.0, 29.3, 34.8, 35.3, 44.0, 46.3, 51.5, 60.4, 68.7, 172.3.

Example 2

N,N-bis[2-(1,2,2,6,6-pentamethyl-4-piperidinyloxycarbonyl)ethyl]cyclohexylamine (Illustrative Compound 2)

To a 300 ml reactor equipped with a magnetic stirrer, a thermocouple and a Dean-Stark condenser were added 5.43 g (20 mmol) of CHADA (not purified) obtained in the same manner as in the [Reaction 1] of Example 1, 18.56 g (50 mmol, 1.25 equivalents) of 1,2,2,6,6-pentamethyl-4-piperidinol, 200 ml of hexane and 0.1 g (4.4 mmol) of lithiumamide. The reaction system was heated under ample stirring to about 70° C. to conduct reaction for 16 hours with removal of methanol distilled by the Dean-Stark condenser. After the given reaction period, the reaction mixture cooled to room temperature was transferred to a separatory funnel, and 300 ml of ether was added before washing three times with 100 ml of $H_2O$. The solution after washing with water was dried over anhydrous magnesium sulfate for about 3 hours, filtered, concentrated to give 10.9 g of a slightly yellowish liquid. Purification of the liquid by chromatography on an alumina column (solvent, $CHCl_3$) gave 9.8 g of a white solid as the target compound (Illustrative Compound 2) (yield, 89.1%).

Physical properties of the compound are as follows:
(1) Melting point: 52.1° C.
(2) Molecular weight: 549 (m/e).

(3) $^1$H-NMR (CDCl$_3$) δ (ppm) 0.93-1.33 (m, 29H), 1.35-1.94 (m, 13H), 2.24 (s, 6H), 2.30-2.48 (m, 5H), 2.78 (t, 4H), 4.97-5.13 (m, 2H).

(4) $^{13}$C-NMR (CDCl$_3$) δ (ppm) 20.5, 26.0, 26.1, 27.9, 29.1, 33.1, 35.1, 45.8, 46.2, 55.0, 60.3, 67.4, 172.2.

Example 3

N-[2-(2,2,6,6-tetramethyl-4-piperidinyloxycarbonyl)-ethyl]dicyclohexylamine (Illustrative Compound 13)

[Reaction 1]

To a 100 ml reactor equipped with a magnetic stirrer, a thermocouple and a condenser were added 10.1 g (56 mmol) of dicyclohexylamine, 50 ml of methanol and 14.4 g (168 mmol, 3.0 equivalents) of methyl acrylate, and the reaction system was heated under ample stirring to 65° C. to conduct reaction at the temperature for 24 hours.

After the given reaction time, the reaction system was cooled to room temperature, and methanol and unreacted methyl acrylate were removed under reduced pressure. The procedure comprising the addition of 30 ml of methanol to the residue and the distillation under reduced pressure was repeated three times to remove completely the methyl acrylate.

The compound obtained was N(2-methoxycarbonylethyl)dicyclohexylamine (referred to hereinafter a DCHAMA) in an amount of 13.7 g (purity, 97%) and a yield of 91%.

[Reaction 2]

To a 300 ml reactor equipped with a magnetic stirrer, a thermocouple and a Dean-Stark condenser were added 2.67 g (10 mmol) of DCHAMA (not purified) obtained in the [Reaction 1] described above, 1.88 g (120 mmol) of 2,2,6,6-tetramethyl-4-piperidinol, 80 ml of heptane and 0.1 g (1.9 mmol) of sodium methoxide. The reaction system was heated under ample stirring to about 100° C. to conduct reaction for 6 hours with removal of methanol distilled by the Dean-Stark condenser. After the given reaction period, the reaction mixture cooled to room temperature was transferred to a separatory funnel, and 200 ml of ether was added before washing three times with 50 ml of H$_2$O. The solution after washing with water was dried over anhydrous magnesium sulfate for about 3 hours, filtered, concentrated to give 4.33 g of pale yellow crystals. Recrystallization of the crystals from acetonitrile gave 3.69 g of white crystals as the target compound (Illustrative Compound 13) (yield, 93.9%).

Physical properties of the compound are as follows:
(1) Melting point: 65.8° C.
(2) Molecular weight: 392 (m/e).
(3) $^1$H-NMR (CDCl$_3$) δ (ppm) 0.92-1.41 (m, 26H), 1.46-2.07 (m, 12H), 2.24-2.64 (m, 4H), 2.86 (t, 2H), 5.07-5.31 (m, 1H).
(4) $^{13}$C-NMR (CDCl$_3$) δ (ppm) 26.1, 26.3, 28.9, 31.8, 34.8, 37.4, 42.3, 43.9, 51.4, 58.0, 68.4, 172.5.

Example 4

N-[2-(1,2,2,6,6-pentamethyl-4-piperidinyloxycarbonyl)-ethyl]dicyclohexylamine (Illustrative Compound 14)

To a 100 ml reactor equipped with a magnetic stirrer, a thermocouple and a Dean-Stark condenser were added 2.67 g (10 mmol) of DCHAMA (not purified) obtained in the same manner as in the [Reaction 1] of Example 3, 2.05 g (12 mmol) of 1,2,2,6,6-pentamethyl-4-piperidinol, 80 ml of heptane and 0.1 g (4.4 mmol) of lithiumamide. The reaction system was heated under ample stirring to about 100° C. to conduct reaction for 12 hours with removal of methanol distilled by the Dean-Stark condenser. After the given reaction period, the reaction mixture cooled to room temperature was transferred to a separatory funnel, and 200 ml of ether was added before washing three times with 50 ml of H$_2$O. The solution after washing with water was dried over anhydrous magnesium sulfate for about 3 hours, filtered, concentrated to give 3.82 g of a pale yellow liquid. Purification of the liquid by chromatography on an alumina column (solvent, CHCl$_3$) gave 3.41 g of a colorless transparent liquid as the target compound (Illustrative Compound 14) (yield, 84.0%).

Physical properties of the compound are as follows:
(1) Molecular weight: 406 (m/e).
(2) $^1$H-NMR (CDCl$_3$) δ (ppm) 0.87-1.33 (m, 24H), 1.41-1.94 (m, 12H), 2.24 (s, 3H), 2.36 (t, 2H), 2.41-2.61 (m, 2H), 2.86 (t, 2H), 4.97-5.12 (m, 1H).
(3) $^{13}$C-NMR (CDCl$_3$) δ (ppm) 20.7, 26.2, 26.4, 28.0, 28.2, 31.8, 33.1, 37.5, 42.4, 46.0, 58.1, 67.4, 172.8.

Example 5

N-[2-(3-benzyl-2,2,6,6-tetramethyl-4-piperidinyloxycarbonyl)ethyl]dicyclohexylamine (Illustrative Compound 17)

To a 100 ml reactor equipped with a magnetic stirrer, a thermocouple and a Dean-Stark condenser were added 2.67 g (10 mmol) of DCHAMA (not purified) obtained in the same manner as in the [Reaction 1] of Example 3, 2.96 g (12 mmol) of 3-benzyl-2,2,6,6-tetramethyl-4-piperidinol, 80 ml of heptane and 0.1 g (4.4 mmol) of lithiumamide. The reaction system was heated under ample stirring to about 100° C. to conduct reaction for 15 hours with removal of methanol distilled by the Dean-Stark condenser. After the given reaction period, the reaction mixture cooled to room temperature was transferred to a separatory funnel, and 200 ml of ether was added before washing three times with 50 ml of H$_2$O. The solution after washing with water was dried over anhydrous magnesium sulfate for about 3 hours, filtered, concentrated to give 5.85 g of a pale yellow liquid. Purification of the liquid by chromatography on an alumina column (solvent, CHCl$_3$) gave 4.07 g of a slightly yellowish liquid as the aimed compound (Illustrative Compound 17) (yield, 84.3%).

Physical properties of the compound are as follows:
(1) Molecular weight: 482 (m/e).
(2) $^1$H-NMR (CDCl$_3$) δ (ppm) 0.91-2.04 (m, 36H), 2.29-3.07 (m, 8H), 4.88-5.09 (m, 1H), 7.01-7.40 (m, 5H).
(3) $^{13}$C-NMR (CDCl$_3$) δ (ppm) 26.3, 26.4, 26.9, 30.7, 31.8, 31.9, 32.8, 33.2, 34.4, 38.0, 40.7, 42.3, 49.2, 49.9, 53.0, 58.3, 69.7, 126.0, 128.4, 128.9, 141.0, 172.2.

In this connection, the substituents in the general formula [I] of the above described compounds are listed in the following table.

TABLE 1

| Ex. No. | Comp. No. | R$^1$ | R$^2$ | R$^3$ | R$^4$ | R$^5$ | X | n |
|---|---|---|---|---|---|---|---|---|
| 1 | 1 | H | H | H | H | | —CH$_2$—CH$_2$— | 1 |
| 2 | 2 | CH$_3$ | H | H | H | | —CH$_2$—CH$_2$— | 2 |
| 3 | 13 | H | H | H | H | | —CH$_2$—CH$_2$— | 2 |

TABLE 1-continued

| Ex. No. | Comp. No. | R¹ | R² | R³ | R⁴ | R⁵ | X | n |
|---|---|---|---|---|---|---|---|---|
| 4 | 14 | $CH_3$ | H | H | H | | $-CH_2-CH_2-$ | 2 |
| 5 | 17 | H | H | H | $-CH_2-R^5$ | $-C_6H_5$ | $-CH_2-CH_2-$ | 2 |

Evaluation Example 1

Photostabilization effect

To 100 parts by weight of polypropylene powder having an intrinsic viscosity of 1.9 measured in tetralin at 135° C. and comprising 98% of isotactic polypropylene was blended with 0.2 part by weight of a sample prepared in any one of Examples 1 to 5, 0.1 part by weight of tetrakis[3-(3,5-di-t-butyl-4-hydroxyphenyl)-propionyloxymethyl]methane and 0.05 part by weight of calcium stearate, and the blend was mixed thoroughly in a mixer followed by melt kneading for pelletization with an extruder having a diameter of 20 mm at a cylinder temperature of 260° C. Pellets thus obtained were subjected to compression molding into a sheet having a thickness of 0.5 mm to make a test piece. Test pieces for control were obtained from sheets prepared in the same manner as above except that SANOL ® LS770 (manufactured by Sankyo K.K., Japan; Comparative Compound 1) or CHIMASSORB ® 944 (manufactured by Ciba-Geigy; Comparative Compound 2) which were commercially available hindered amine type photostabilizers were used in place of the compounds prepared in Examples 1 to 5.

These test pieces were irradiated with light at a black panel temperature of 80° C. with a Weather-O-Meter, 65/XW-WR Model manufactured by Atlas Co., to compare the times required for the deterioration of respective test pieces. The results obtained are shown in Table 1.

As apparent from the results shown in Table 2, all of the cyclohexylamine derivatives according to the present invention exhibit excellent stabilizing effect (i.e. longer time until deterioration) as compared with the Comparative Compounds (Nos. 7, 8).

TABLE 2

| No. | Compound Added | Time until deterioration (hour) |
|---|---|---|
| 1 | none | 155 |
| 2 | Illustrative Compound 1 | 720 |
| 3 | Illustrative Compound 2 | 840 |
| 4 | Illustrative Compound 13 | 620 |
| 5 | Illustrative Compound 14 | 760 |
| 6 | Illustrative Compound 17 | 680 |
| 7 | Comparative Compound 1 | 500 |
| 8 | Comparative Compound 2 | 320 |

Evaluation Example 2

Bleedout

Upon weathering test for 300 hours in a Weather-O-Meter described herein for the sheets respectively containing the compounds in Examples 1 to 5, Illustrative Compounds 1 to 5, and the sheet containing Comparative Compound 1 (SANOL ® LS770), no bleeding was observed on the sheets containing the Illustrative Compounds 1 to 5, but there was bleed found as impalpable powder on the surface of the sheet in the case of Comparative Compound 1, where the bleed was confirmed by wiping the sheet.

What is claimed is:

1. A cyclohexylamine compound represented by the general formula:

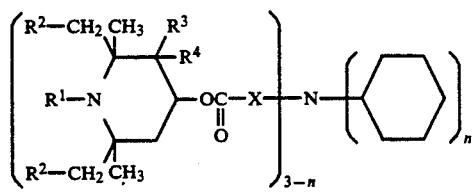

wherein R¹ represents a hydrogen atom, an alkyl group having 1 to 4 carbon atoms, an acyl group of the formula $-C(=O)-R^6$, in which R⁶ represents a $C_1-C_6$ alkyl group or a phenyl group, or an phenylalkyl group of the formula

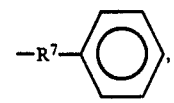

in which R⁷ represents a $C_1-C_4$ alkylene group, and R² each represents a hydrogen atom or an alkyl group having 1 to 4 carbon atoms, R³ and R⁴ both represent a hydrogen atom, or one of R³ and R⁴ represents a hydrogen atom and the other represents a group $-CH_2-R^5$, or R³ and R⁴ together form a group $=CH-R^5$, in which R⁵ represents an unsubstituted or $C_1-C_4$ alkyl substituted phenyl group, a 2-furyl group, a cyclohexyl group or a 2-tetrahydrofuryl group, X represents an alkylene group having 1 to 3 carbon atoms, and n denotes 1 or 2.

2. A cyclohexylamine compound according to claim 1, wherein R¹ represents a hydrogen atom or a methyl group.

3. A cyclohexylamine compound according to claim 1, wherein R² represents a hydrogen atom or a methyl group.

4. A cyclohexylamine compound according to claim 1, wherein both of R³ and R⁴ represent a hydrogen atom.

5. A cyclohexylamine compound according to claim 1, wherein R³ represents a hydrogen atom and R⁴ represents a benzyl group.

6. A cyclohexylamine compound according to claim 1, wherein R³ represents a hydrogen atom and R⁴ represents a cyclohexylmethyl group.

7. A cyclohexylamine compound according to claim 1, wherein X represents a group $-CH_2-CH_2-$.

8. A cyclohexylamine compound according to claim 1, wherein n denotes 1.

9. The cyclohexylamine compound of claim 1, wherein R¹ is an acyl group is an acetyl group or a benzoyl group.

10. The cyclohexylamine compound of claim 1, wherein said phenylalkyl group is a benzyl group or a 1-phenylethyl group.

11. The cyclohexylamine compound of claim 9, wherein said phenylalkyl group is a benzyl group or a 1-phenylethyl group.

12. N,N-bis[2-(1,2,2,6,6-pentamethyl-4-piperidinyloxy-carbonyl)ethyl]cyclohexylamine.

13. N-[2-(1,2,2,6,6-pentamethyl-4-piperidinyloxycarbonyl)ethyl]dicyclohexylamine.

14. N-[2-(3-benzyl-2,2,6,6-tetramethyl-4-piperidinyloxycarbonyl)ethyl]dicyclohexylamine.

15. N-[2-(3-cyclohexylmethyl-2,2,6,6-tetramethyl-4-piperidinyloxycarbonyl)ethyl]dicyclohexylamine.

* * * * *